Figure 1:
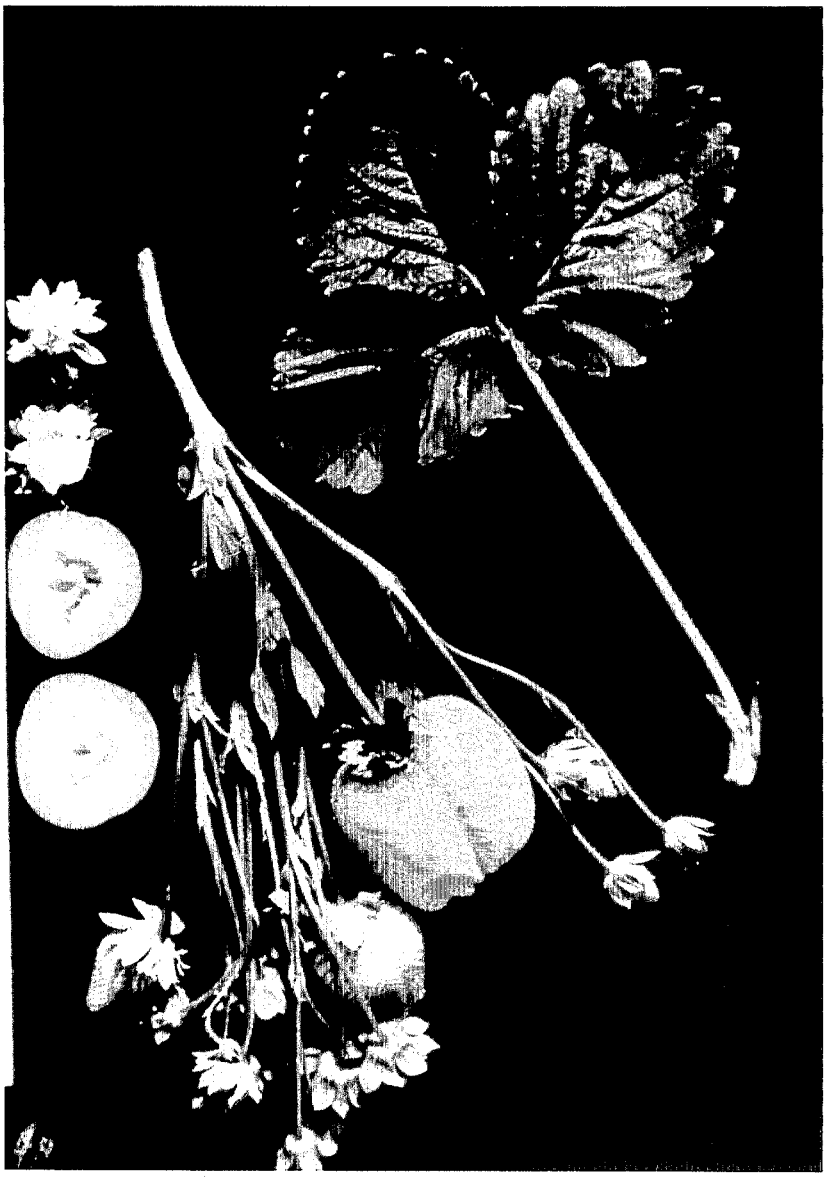

United States Patent [19]

Johnson, Jr. et al.

[11] Patent Number: Plant 5,840

[45] Date of Patent: Dec. 23, 1986

[54] STRAWBERRY PLANT—'MR. P'

[75] Inventors: Harold A. Johnson, Jr.; Amado Q. Amorao, both of Watsonville, Calif.

[73] Assignee: Driscoll Strawberry Associates, Inc., Watsonville, Calif.

[21] Appl. No.: 699,965

[22] Filed: Feb. 8, 1985

[51] Int. Cl.[4] ..... A01H 5/03

[52] U.S. Cl. ..... Plt./49

[58] Field of Search ..... Plt./49

*Primary Examiner*—R. E. Bagwill

*Attorney, Agent, or Firm*—Townsend and Townsend

[57] ABSTRACT

A new and distinct everbearing variety of strawberry plant characterized by fruit which is consistently large, especially for an everbearer, that is medium wedge to conic in outline and has a noticeably good flavor. The plant is also characterized by its ability to produce many crowns by the time the main crop is harvested after being planted if favorable soil moisture and nutrition is maintained. Its cropping is characterized by a heavy peak in production that occurs in the central coast region of California during August if planted during late January, February or March.

1 Drawing Figure

This invention relates to a new and distinct variety of strawberry plant which is the result of a cross of the Driscoll selection B6.117 and the Driscoll selection D5.23. This new variety has been given the name "Mr. P".

The seedlings resulting from the aforementioned cross were grown and asexually multiplied in Shasta County, Calif. and tested in the fruiting beds on the property of growers of the Driscoll Strawberry Associates, Inc. Clones of the seedlings were also held at the Shasta County nursery of Driscoll Strawberry Associates, Inc. One plant was selected from the aforementioned group of seedlings and further asexually reproduced by runners in the Shasta County nursery. Tests followed in various parts of California during intervening seasons on various properties of grower members of the Driscoll Strawberry Associates, Inc. These tests indicated the merits of the novel plant and resulted in its selection as a promising test variety.

In the drawing:

FIG. 1 illustrates plant parts of the new everbearing variety which are typical in size, shape, and color.

Referring to FIG. 1, the berry is shown in cross sections illustrating flesh color and core cavity. The primary berry attached to the inflorescence is typical during the last week in July of plants that were planted during February. Primary berries are often wedged in shape with some whiteness at the apex and may or may not have the longitudinal furrow shown in the illustration. Secondary and tertiary berries tend to be more conic as is also illustrated. Four secondary peduncles and the pedicel holding the primary berry originating at the axil formed by the union of the four peduncles are shown. The pedicel may originate from the side of one of the secondary peduncles, but an equal amount may originate at the axil. The leaf present is typical, and may or may not have bracts present on the petiole. The calyxes present are typical, with serrated overlapping sepals present on primaries. There are less serrations on the sepals of secondary and tertiary berries than on primaries.

The plant of this novel variety is medium in size and can become large for an everbearer if allowed to have adequate moisture and nutritional needs satisfied during the period when the plant is being established before cropping. It has the ability to produce many crowns per plant, and also to continue good fruit size with an abundance of berries produced per crown. This new variety also has the ability to produce its peak production during August when planted in February. It gradually drops in production during September and October.

Some of the distinguishing characteristics are its very vigorous multi-crown plant when given consistent moisture and nutrition from the time of planting. This is usually larger than the Driscoll E24 variety, U.S. Plant Pat. No. 4,988. Also the large consistent fruit size of even secondary and tertiary berries is quite distinguishing, especially for an everbearer. Its crown crop fruit are noticeably large and attractive, larger than that of E24 and the Driscoll variety 'Heidi,' U.S. Plant Pat. No. 3,123. The outstanding flavor is also distinguishing. 'Heidi' and E24 are considered good flavored, but during 1983 and 1984, panelists rated 'Mr. P' superior when all ratings for those two years were averaged. Under nursery conditions 'Mr. P' performs like a true everbearer, cropping heavily under very warm conditions during both long and short day lengths with relatively few runners per mother plant in contrast to E24. E24 isn't considered a good runner producer, but it is superior to 'Mr. P'. Also, under the high humidity of the nursery propagation it becomes susceptible to several leafspot organisms, and a vascular disease not identified at this time. In the cooler fruiting beds, leafspot diseases do not express themselves and vascular collapse infection doesn't appear to move from plants infected to those non-infected. Also, under cooler fruiting bed conditions runners are more abundant than at the nursery.

Other characteristics that help distinguish 'Mr. P' from other varieties are its large leaflets similar to 'Heidi' but which are slightly larger and thicker than E24. The leaflets, however, do vary from 'Heidi'. One difference is the more sharply pointed apex of the leaflet serrations of 'Heidi' in contrast to 'Mr. P'.

The fruit is distinguished from 'Heidi' and E24, but is closer to the 'Heidi' fruit shape. 'Mr. P' has seed that are more exerted than E24, and the main crop primaries are more prone to produce longitudinal furrows as well as being larger and having wider shoulders near the calyx. The calyx is generally clasping to the fruit in contrast to E24, and the fruit doesn't become necked with a noticeable space without seed where the fruit is attached to the calyx, which is often the case with E24. Pedicels of the fruit are thicker and larger than that of E24. Hair on the pedicels are abundant and perpendicular to the pedicel similar to E24, but in contrast to 'Heidi' whose hair is irregularly parallel to the pedicel. If planted at the same time, and given adequate moisture and nutrition, the peak of production is later with 'Mr. P' than E24. Both varieties, however, will produce in May, June and July, with peaks in late July and August, and a drop in production during September and October, but the peak is later with 'Mr. P'.

The firmness of the skin and flesh, and appearance of the fruit of 'Mr. P' is considered good, superior to E24. 'Mr. P' holds its seed equal to the surface or slightly exerted in contrast to E24 whose seed are often sunken, and having areas near the calyx that are without seed making the skin more vulnerable to injury. Holding-tests have shown 'Mr. P' to be equal to 'Heidi' during most tests.

'Mr. P' is more susceptible than 'Heidi' or E24 to injury from thrip feeding causing a bronzing and lack of gloss. During harvest, if 'Mr. P' doesn't receive adequate irrigation needs it will stem (the calyx will not remain with the fruit) easily during warm weather.

This new variety has a mild, pleasant strawberry odor, but not distinct from E24 or 'Heidi'. 'Mr. P' hasn't been tested against the Verticillium wilt or the red stele pathogens. As a seedling and selection it withstood the natural invasion of certain virus components found in central California without losing its ability to produce.

The varietal characteristics described below in detail were observed during the first fruiting season. Observations were made during July and August in the Watsonville area of California which is a cool coastal area near the Pacific Ocean. The color terminology is in accordance with the Munsell Color System.

Plant: Medium to large in size developing multiple crowns if given adequate moisture and nutrition from the planting day till the maturity of the main crop. The plant may not reach its potential if grown in soil where a high salt level is present.

Leaves: Medium to large in size. The mature central leaflet is usually 6 to 9 cm. in width and length. Petiole length can become long usually 20 to 28 cm. when mature. Less than half of the petioles develop bracts. The leafleats are moderately rugose and are held irregularly upward. The serrations of leaflets are only moderately deep or acute at the apex as compared to other varieties such as 'Heidi'. The color of the upper side of the leaflet is 3.1 G 2.6/7.1.

Runners: More than one runner per plant can be expected if the variety is planted in the fruiting bed during February and March after an early January digging. Thus far under the hot humid conditions of the nursery, 'Mr. P' variety produces runners in low amounts per mother plant.

Inflorescence: Medium in length and abundant per plant, with mostly two peduncles per inflorescence but fewer or more may be present. Peduncles and pedicels are considered thick and long in comparison to other everbearing varieties. The hair on pedicels holding tertiary flowers is perpendicular to the pedicel. A near equal amount of pedicels holding the primary berry originate from the axil formed by the union of peduncles or form one of the peduncels. Flowers can be observed above the plant and are moderately abundant during most of the fruiting season. Anthers produce an abundance of pollen.

Fruit: Primary fruit of the crown and main crop are large, average 45 mm. in length and width. Secondary and tertiary fruit are smaller than primaries, but are still considered large especially for everbearing fruit. The shoulders of the fruit are rounded, not necked. The primary berries in outline are mostly medium wedge as described in the U.S.D.A. Bulletin 1043, but secondary and tertiary fruit tend to be more conic with less longitudinal furrows present. Primary fruit from the crown crop is less furrowed than those of the main crop. Other than the longitudinal furrows the surface is relatively smooth, and the skin and flesh are considered firm with the seed held equal to or slightly exerted above the surface of the epidermis. Good holding test ratings have reflected the firmness of the fruit. The appearance of the surface is considered attractive with a good gloss usually present except when thrip have been allowed to build up in large numbers, and have fed on the flowers and fruit, when the surface becomes bronzed in appearance due to the feeding of the thrip. The dessert quality of the fruit has rated high in all of the panel taste tests given. The surface color is mostly 6.6 R 2.9/9.7 and the flesh color near the epidermis is 6.8 R 4.6/16.5.

Calyx: Primaries medium to large with sepals that are serrated and overlapping. The calyx is usually clasping the fruit and is not reflexed if not touching the fruit. It may, however, become reflexed because of rounded shoulders of berries that often produce sepals and pedicels that may attach to the fruit below the surface when viewing the profile of a berry from the side. Color of the sepal when viewing the side facing the fruit is 0.8 G 5.2/13.5.

We claim:

1. The new and distinct variety of strawberry plant herein described and illustrated and identified by the characteristics enumerated above together with the parts thereof.

* * * * *